United States Patent [19]

Marx

[11] Patent Number: 5,411,885
[45] Date of Patent: May 2, 1995

[54] METHODS FOR TISSUE EMBEDDING AND TISSUE CULTURING

[75] Inventor: Gerard Marx, New York, N.Y.

[73] Assignee: New York Blood Center, Inc., New York, N.Y.

[21] Appl. No.: 168,683

[22] Filed: Dec. 17, 1993

[51] Int. Cl.6 .................. C12N 5/00; A61K 37/547; A61K 37/553; A61K 37/00
[52] U.S. Cl. ............... 435/240.2; 424/94.64; 514/2
[58] Field of Search ............. 424/94.64, 572, 422, 424/484; 530/381; 514/2; 435/240.2

[56] References Cited

U.S. PATENT DOCUMENTS

| | | | |
|---|---|---|---|
| 4,414,976 | 11/1983 | Schwarz et al. | 128/334 R |
| 4,427,650 | 1/1984 | Stroetmann | 424/46 |
| 4,485,096 | 12/1984 | Bell | 424/95 |
| 4,627,879 | 12/1986 | Rose et al. | 106/124 |
| 4,642,120 | 2/1987 | Nevo et al. | 623/16 |
| 4,904,259 | 2/1990 | Itay | 623/16 |
| 5,053,050 | 10/1991 | Itay | 623/16 |
| 5,290,552 | 3/1994 | Sierra et al. | 424/94.64 |
| 5,290,918 | 3/1994 | Bui-Khac | 530/381 |

FOREIGN PATENT DOCUMENTS 2081090  2/1982  United Kingdom .

OTHER PUBLICATIONS

Kalus, M. et al., Cancer 22:507–516 (1968), "The Growth of Tumors in Matrix Cultures".
Kalus, M. et al., Arch. Path., 86:52–59 (1968), "Organ Tissue Culture on a Three-Dimensional Matrix of Human Fibrin Foam".
Burnouf-Radosevich, M. et al., Vox Sang, 58:77–84 (1990), "Biochemical and Physical Properties of a Solvent-Detergent-Treated Fibrin Glue".
Pinkle, H. et al. Thrombosis and Haemostasis, 65:444–450 (1991) "Thrombin-Like Enzymes from Snake Venomm: An Inventory".
Marx, G. et al., Blood Coagulation and Fibrinolysis, 4:73–78 (1993), "Kinetic and Mechanical Parameters of Pure and Cryoprecipitate Fibrin".
Hatzfeld, J. A. et al., Proc. Natl. Acad. Sci. USA, 79:6280–6284 (1982), "Fibrinogen and its Fragment D Stimulate Proliferation of Human Hemopoietic Cells In Vitro".
Shuman, M. A., Annals N.Y. Acad. Sci., vol. 485, pp. 228–239 (1986), "Thrombin-Cellular Interactions".

Primary Examiner—Douglas W. Robinson
Assistant Examiner—Kristin Larson
Attorney, Agent, or Firm—Elizabeth M. Barnhard; Bryan Cave

[57] ABSTRACT

Methods of embedding and culturing tissue employing a fibrin glue composition of 2 to 100 mg/ml fibrinogen, 1 to 200 U/ml fibrinogen-activating enzyme, and 1 to 30 mM Ca(II) compound, are disclosed.

9 Claims, 1 Drawing Sheet

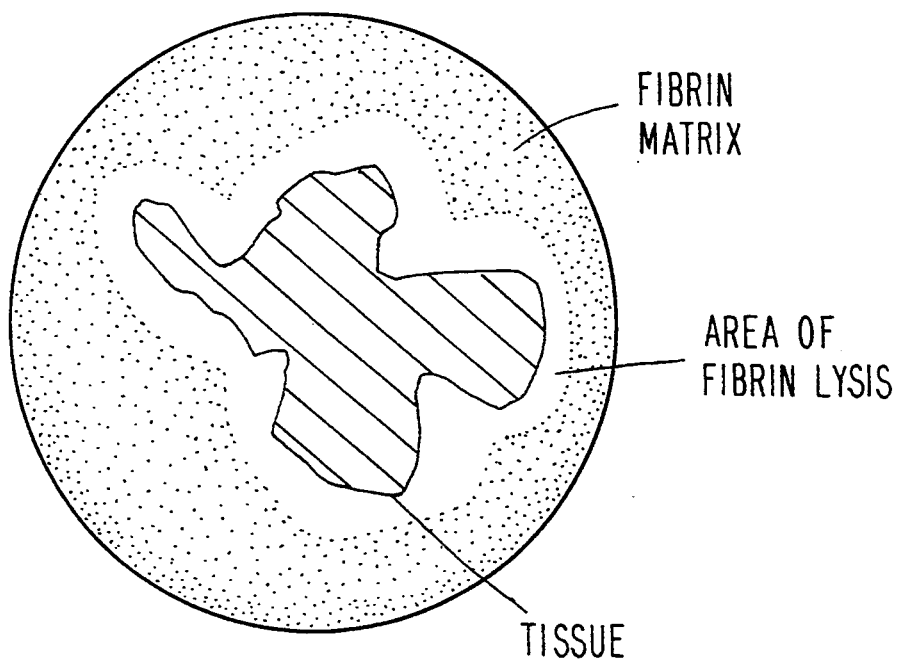

METHODS FOR TISSUE EMBEDDING AND TISSUE CULTURING

FIELD OF THE INVENTION

This invention relates to methods of embedding and culturing tissue employing a fibrin glue composition comprising fibrinogen, fibrinogen-activating enzyme, and a calcium compound.

BACKGROUND OF THE INVENTION

The loss or failure of an organ or tissue can have a severe impact on the health and well-being of the affected person or animal. To understand the role of a particular organ or tissue in the body, how it grows, and its response to different agents, studies are done on samples of organ or tissue which are maintained in culture. The term "tissue" is used hereafter to refer to both organs and tissues. A problem in tissue culture studies is maintaining viability of the sample in culture. Another problem is the difficulty of routinely being able to prepare sections of tissue of a defined size for culturing. A lack of uniformity of the size of tissue sections means that accurate comparisons of results cannot be made.

Tissue samples are usually embedded by fixing the tissue in formalin and then embedding in paraffin. Other fixatives that may be used to preserve tissue samples include mercuric chloride, picric acid, glutaraldehyde, Bouin's fluid, and Zenker's formalin (Helly's fluid). In addition to paraffin, plastic resins may be used for embedding the tissue samples. Disadvantages of these fixatives and embedding materials arise from trauma to the tissue, toxicity of the embedding material, and difficulty in obtaining sections of defined size, particularly of soft tissue.

Fibrinogen is mitogenic and stimulates cell growth and viability. A human fibrin foam prepared by lyophilization of a solution of human fibrinogen has been used to culture tumors by placing pieces of tumor on top of $10 \times 10 \times 3$ millimeter semi-cubes of fibrin foam sitting in culture medium. Kalus, M. et al., Cancer 22:507–516 (1968); Kalus, M. et al., Arch. Path. 86:52–59 (1968). A disadvantage of this method is that only one side of the tissue sample is in contact with the fibrinogen, which minimizes the stimulatory effect of the fibrinogen. (All of the documents cited or otherwise referenced herein are incorporated herein in their entirety for all purposes.)

Fibrin glue, usually made from freeze-dried plasma fibrinogen/factor XIII concentrate and thrombin, has been used in surgical applications such as replacement of sutures in skin grafts, nerve and vessel anastomoses, and surgery of parenchymal tissues of liver, lung, or spleen. In Itay U.S. Pat. Nos. 4,904,259 and 5,053,050, bone and cartilage are repaired by implanting a proliferating chondrocyte cell structure having phenotypic capability embedded in a biological glue consisting of 10–30% serum containing growth factors, 100 to 150 mg/ml fibrinogen, 60 to 90 U/ml thrombin, 60 mM $CaCl_2$, and 2,000 U/ml (KIU) aproprotein.

There is a continuing need for methods for embedding and culturing tissues that are non-toxic to the tissue, that allow improved sectioning of the tissue with less trauma to the tissue, and that allow better diffusion of tissue culture fluid to the sectioned tissue.

SUMMARY OF THE INVENTION

The methods of this invention satisfy those needs and have other advantages that will be apparent to those skilled in the art. The present invention provides methods of embedding and culturing tissue employing a fibrin glue composition comprising 2 to 100 milligrams/milliliter (mg/ml) fibrinogen, 1 to 200 International Units/milliliter (U/ml) fibrinogen-activating enzyme, and 1 to 30 millimolar (mM) Ca(II) compound. As used herein, "Ca(II) compound" means a compound containing calcium in which the calcium nominally has a valence of +2, e.g., calcium chloride. The calcium compound can be any calcium salt. The fibrin glue composition can be used to embed tissue, which embedded tissue can be cut into sections 60 to 1,000 microns thick, and to culture tissue.

One advantage of the fibrin glue composition employed by the methods of this invention is that it is non-toxic to the tissue being embedded and/or cultured in it. Another advantage is that the fibrin glue composition imparts useful mechanical properties to the tissue embedded within it, which results in improved sectioning of the embedded tissue with less trauma to the embedded tissue.

An advantage of the methods of embedding tissue in the fibrin glue composition is that the mechanical properties of the fibrin glue composition can be manipulated to provide the appropriate resistance to cutting for the type of tissue to be embedded and sectioned.

The present invention also provides a method of culturing tissue embedded in the fibrin glue composition in which embedded tissue can accurately be cut into uniformly thick sections ranging in size from 60 to 1000 microns and the sections cultured. One advantage of this method is that the fibrin glue composition allows better diffusion of tissue culture fluid to the subsurface cells of the sectioned tissue, thereby minimizing tissue necrosis. Another advantage is that the fibrinogen and thrombin components of the fibrin glue, or their degradation products, are mitogenic and have a stimulatory effect on cell viability and growth of the cells of the sectioned tissue.

Other features and advantages of this invention will be apparent to those skilled in the art.

BRIEF DESCRIPTION OF THE DRAWINGS

To facilitate further discussion of the invention, the following drawing is provided in which:

FIG. 1 is a schematic diagram of the viability measurement of a cultured tissue section embedded in the fibrin glue composition, showing a cleared area that develops around the viable, cultured tissue.

DETAILED DESCRIPTION OF THE INVENTION

In the present invention, tissue may be embedded using as a matrix a fibrin glue composition comprising 2 to 100 milligrams (mg) of fibrinogen per milliliter (ml) of glue composition, 1 to 200 International Units (U) of fibrinogen-activating enzyme per milliliter of glue composition, and one or more Ca(II) compounds in amounts sufficient to provide a calcium concentration in the glue composition of 1 to 30 millimolar (mM). Any tissue from any biological organism (e.g., human, non-human animal) may be used. The tissue can be fragments or complete organs such as heart or liver, tumors, or other types of tissue such as skin, or biopsy samples.

Commercially available fibrinogen may be used in the fibrin glue composition and is available from Sigma Chemical Co., St. Louis, Mo. and Kabi, Stockholm, Sweden. Fibrinogen from fibrin sealant kits sold in Europe under the trade names Tisseel TM (Immuno, Austria) and Beriplast TM (Behringwerke, Marburg, Germany) may also be used. Cryoprecipitate fibrinogen prepared by blood banks may also be used in the fibrin glue composition. The fibrinogen is preferably human fibrinogen that has been virally inactivated (e.g., solvent/detergent-treated fibrinogen, hereafter "S/D fibrinogen"; see, e.g., U.S. Pat. Nos. 4,540,573 and 4,764,369; Burnouf-Radosevich, M. et al., Vox Sang 58:79–84, "*Biochemical and physical properties of solvent-detergent treated fibrin glue*"). The mechanical properties of the fibrin glue and its resistance to cutting, i.e., breaking strength, may be adjusted to the tissue being embedded in the fibrin glue by altering the fibrinogen concentration. For soft tissues, such as liver, it is preferable to use fibrin glues with a low fibrinogen content of 2–20 mg/ml. For tough tissues, such as skin, it is preferable to use fibrin glues with a high fibrinogen content of 20–100 mg/ml. By adjusting the mechanical properties of the fibrin glue to the tissue being embedded, better sections can be obtained with less trauma to the embedded tissue.

The fibrinogen-activating enzyme may be thrombin, batroxobin, thrombocytin, ancrod, or other thrombin-like enzymes. Thrombin-like enzymes from snake venoms that coagulate fibrinogen are described in Seegers, W. H. & Ouyang, C., Handbook of Experimental Pharmacology 52:684–740 (1979), "Snake venoms and blood coagulation"; Stocker, K. et al., Thrombos. Diathes. Haemorrh. Suppl. 54:361–369 (1973)., "Reptilase as a defibrinogenating agent"; Niewiarowski, S. et al., Biochem. 18:3570–3577 (1979), "Thrombocytin, a serine protease from Bothrops atrox venom II"; Stocker K. et al., Toxicon. 20:265–273 (1982), "Thrombin-like snake venom proteinases"; and Pirkle, H. et al., Thrombos. Haemostas. 65:444–450 (1991), "Thrombin-like enzymes from snake venoms: an inventory." It is preferred to use thrombin as the fibrinogen-activating enzyme, and more preferably human thrombin which has been virally inactivated (e.g., solvent-detergent-treated thrombin).

When thrombin is the fibrinogen-activating enzyme, the preferred ranges for the components of the fibrin glue composition are 20 to 40 mg/ml fibrinogen, 2 to 20 U/ml thrombin, and 2 to 15 mM Ca(II) compound (preferably calcium chloride).

Growth-modulating activity of the embedded tissue may also be modified or controlled by including biologically active materials in the fibrin glue matrix, such as growth factors, peptides, hormones, drugs, minerals, transition metal cations, or mixtures thereof.

To embed the tissue, the tissue is preferably entirely immersed in the fibrin glue while the fibrin glue is in a fluid state. The length of time in which the fibrin glue will remain fluid is dependent upon the concentrations of fibrinogen and the fibrinogen-activating enzyme in the fibrin glue. When the fibrin glue sets, it forms a gel surrounding the tissue. The embedded tissue may then be sliced into sections that can range in size from 60 to 1000 microns. The sections can be maintained in suspension cultures or further encased in fibrin glue to surround all sides of the section with fibrin glue and then maintained in tissue culture medium or cryopreserved until ready to use as described in Fisher, R. et al., "Cryopreservation of pig and human liver slices," Cryobiology 28:131–142 (1991).

The fibrin glue may be prepared by premixing the fibrinogen with the Ca(II) compound, adding the tissue to be embedded, and then adding the fibrinogen-activating enzyme. After a suitable period of time, usually about one minute, this mixture may then be gently mixed and allowed to stand at room temperature for a suitable period of time, e.g., half an hour, until the resulting fibrin glue sets sufficiently and embeds the tissue.

The fibrin glue may also be prepared by mixing fibrinogen and the Ca(II) compound with a low level of the enzyme (for example, thrombin), e.g., in the range of 0.5 to 2.0 U/ml, and then agitating the mixture mechanically or with air or nitrogen for about 15 seconds until there is much bubbling. The tissue to be embedded is then contacted with the glue mixture while the mixture is still fluid and bubbly, preferably by immersing the tissue into the glue mixture. Within a few minutes the bubbly mixture will set and form a fibrin glue foam around the tissue. The tissue encapsulated in the fibrin glue foam is then allowed to stand for a suitable period of time, e.g., one hour, at room temperature so that the glue foam completely sets and embeds the tissue.

Regardless of how embedded in accordance with this invention, the embedded tissue can then be sliced using a tissue slicer, which is preferably maintained under sterile conditions. Embedding tissue in the fibrin glue of the present invention enables the tissue to be sliced to a thickness that permits the optimal diffusion of nutrients and gases within the tissue slice and thereby minimizes tissue necrosis. Section thickness of the fibrin glue embedded tissue may be varied from 60 to 1,000 microns. This thickness range allows good diffusion of nutrients and gases to the sub-surface cells during tissue culturing of the section. Diffusion of nutrients and gases is also aided by the open network in the fibrin glue.

Section slices may be cultured under sterile conditions using standard tissue/organ culture methods, such as the method of Rheinwald, J. G., and Green. H. published in Cell, 6:331–334 (1975). Preferably the slices are transferred to multiwell petri dishes containing antibiotics and tissue culture medium appropriate for the tissue being cultured. Techniques which may be used for culturing organ slices are described in Smith, P. F. et al., Life Sciences 36:1367–75 (1985), "*Dynamic organ culture of precision liver slices for in vitro toxicology*"; and Connors, S. et al., "*Evaluation of organic nephrotoxins using rabbit renal cortical slices*", Alternative Methods in Toxicology, Vol. 6 (1988) (A .M. Goldberg, Ed.). Typically the cultures are incubated at 37° C. under a $CO_2$ incubator (95%-$O_2$, 5%-$O_2$) with gentle shaking. If the section slices are to be cultured at a later time, the section slices may be cryopreserved until such time.

Alternatively, before placing a section slice made using this invention into tissue culture medium, the section slice may be further encased in fibrin glue using the embedding procedure described above so that all surfaces of the sliced tissue are covered with fibrin glue. The fibrin glue-encased tissue section may then be placed into suitable tissue culture medium and cultured as discussed above.

To determine viability of the embedded tissue, a chromogenic substrate for plasmin is used. The tissue section is removed from the tissue culture medium and washed two times in saline, PBS, or tris buffer. If there has been cell growth and the section is viable, there will be a clear zone between the tissue and the surrounding fibrin glue due to fibrin lysis. Homminga, G. N. et al., Acta Orthop. Scand. 64:441–445 (1993), "*Chondrocyte behavior in fibrin glue in vitro*". This clear zone signifies secretion of plasminogen activator by viable cells. FIG. 1 shows a developed clear zone between the tissue and the surrounding fibrin glue. Alternatively, the washed section is incubated in S2251 substrate (H-D-Valyl-L-leucyl-L-lysine-p-nitroaniline dihydrochloride, available from Kabi, Stockholm, Sweden) and then checked for the appearance of a colored zone between the tissue and the surrounding fibrin glue.

The following examples illustrate use of the present invention.

EXAMPLE 1

Embedding and Culturing of Tissue in Fibrin Glue

The needle-affixing end of a sterile 10 ml plastic syringe (17 mm ID, 65 mm long) was cut off and the plunger was removed and set aside, leaving only the barrel. The cut end of the barrel of the syringe was sealed with stretched, moisture-proof, self-sealing, flat wrapper or film (e.g., PARAFILM ® wrapper, American Can Packaging, Inc.) to prevent leakage when liquid was introduced.

A 5×10 mm fragment of freshly excised mouse liver was washed in sterile saline. The liver fragment was placed into the syringe barrel onto the stretched film at the bottom of the syringe barrel. 2 ml Kabi Grade L fibrinogen (42 mg/ml) was poured into the syringe barrel so that the liver fragment was entirely immersed in the solubilized fibrinogen. 100 ul of 10 U/ml thrombin with Ca(II) was added to the solution in the syringe barrel. The solution was gently mixed with a plastic Pasteur pipette two times and allowed to stand at room temperature for half an hour for the fibrin glue to gel and set. The purpose of stirring is to mix the components.

The stretched film was removed and a 21 gauge syringe needle was inserted between the fibrin glue mass containing the liver fragment and the plastic syringe barrel to loosen any fibrin adhering to the barrel. The plunger was placed back into the top of the syringe barrel and then gently depressed to push out the cylindrical fibrin glue mass in which the liver fragment was embedded.

Sections of the embedded liver fragment were cut from the fibrin glue mass utilizing a tissue slicer maintained under sterile conditions. The sections were 60–1000 microns thick. The sections were then transferred to a petri dish and maintained under standard tissue/organ culture conditions with Dubelco's modified Eagle Medium and 10,000 U penicillin and streptomycin in 5% $CO_2$ in air at a temperature of 37° C, with gentle shaking.

Viability and cell growth were measured by monitoring the dissolution of the fibrin glue surrounding the sectioned liver fragment. Viability was measured daily using either a chromogenic substrate for plasmin or examining the section microscopically. Clear zones were found, respectively, around the cultured, sectioned, fibrin glue-embedded, skin fragment and heart fragment, indicating viability and cell growth of the sectioned organ fragments.

EXAMPLE 2

Alternative Method of Embedding and Culturing Of Tissue in Fibrin Glue

The procedures of Example 1 were employed with the following variations.

2 ml of fibrinogen (34 mg/ml) was poured into the syringe barrel and agitated mechanically (by vortex or shaking) for 15 seconds to induce bubbling.

While this mixture was still fluid and bubbly, a 5×10 mm fragment of freshly excised and washed liver was dropped into the bubbly, still fluid mixture. Thereafter, thrombin and Ca(II) were added and mixed. After a few minutes, the bubbly mixture set and formed a fibrin glue foam. This fibrin glue foam was allowed to stand for one hour at room temperature. The fibrin glue foam may also be allowed to stand for one hour at 37° C.

After one hour, the fibrin glue foam containing the liver organ fragment was removed, sectioned, and cultured as described in Example 1. Viability was measured as previously described in Example 1. Microscopic examination indicated viability and growth.

The above description is meant to be illustrative only of the present invention and not limiting thereof. Variations and modifications will be apparent to those skilled in the art and the claims are intended to cover all modifications and variations falling within the true spirit and scope of the invention.

I claim:

1. A method for embedding tissue in vitro comprising the steps of:
   (a) preparing a solution of fibrinogen, wherein the amount of fibrinogen ranges from 2 to 100 mg/ml;
   (b) contacting a tissue with the solution of step (a);
   (c) adding to the solution of step (b) a Ca(II) compound in an amount ranging from 1 to 30 mM and a fibrinogen-activating enzyme in an amount ranging from 0.5 to 200 U/ml; and
   (d) allowing the solution contacting the tissue to stand until the solution forms a gel and embeds the tissue.

2. The method for embedding tissue of claim 1, wherein the Ca(II) compound is added to the solution of step (a) instead of to the solution of step (b).

3. The method for embedding tissue of claim 1, wherein the amount of Ca(II) compound is from 2 to 15 mM.

4. The method for embedding tissue of claim 1, wherein the Ca(II) compound is calcium chloride.

5. The method for embedding tissue of claim 1, wherein the fibrinogen-activitating enzyme is thrombin.

6. A method for embedding tissue in vitro comprising the steps of:
   (a) preparing a solution of fibrinogen, Ca(II) compound, and a fibrinogen-activating enzyme, wherein the amount of fibrinogen ranges from 2 to 100 mg/ml, the amount of Ca(II) compound ranges from 1 to 30 mM, and the amount of the fibrinogen-activating enzyme ranges from 0.5 to 100 U/ml;
   (b) agitating the solution of step (a) to induce bubbling in the solution;
   (c) contacting a tissue with the solution of step (b); and
   (d) allowing the solution of step (c) to stand until the solution gels and embeds the tissue.

7. The method for embedding tissue of claim 6, wherein the fibrinogen-activating enzyme is thrombin and the amount of thrombin is 0.5 to 2 U/ml.

8. A method for culturing tissue comprising the steps of:
(a) embedding tissue in a fibrin glue composition comprising 2 to 100 mg/ml fibrinogen, 0.5 to 200 U/ml fibrinogen-activating enzyme, and 1 to 30 mM Ca(II) compound;
(b) cutting the fibrin glue-embedded tissue into sections ranging from 60 to 1,000 microns in thickness; and
(c) culturing the sections of fibrin glue-embedded tissue in tissue culture medium.

9. The method for culturing tissue of claim 8, wherein the fibrin glue composition of step (a) further comprises a growth-modulating biologically active compound.

* * * * *